United States Patent [19]

Wimmer et al.

[11] Patent Number: 5,012,013

[45] Date of Patent: Apr. 30, 1991

[54] PROCESS FOR THE PURIFICATION OF ALKYLENE OXIDE ADDUCTS

[76] Inventors: Ignaz Wimmer; Siegfried Billenstein, both c/o Hoechst Aktiengesellschaft, P.O. Box 80 03 20, D-6230 Frankfurt am Main 80, Fed. Rep. of Germany

[21] Appl. No.: 516,133

[22] Filed: Apr. 26, 1990

[30] Foreign Application Priority Data

Apr. 27, 1989 [DE] Fed. Rep. of Germany ....... 3913937

[51] Int. Cl.[5] .............................................. C07C 41/34
[52] U.S. Cl. .................................................... 568/621
[58] Field of Search ........................................ 568/621

[56] References Cited

FOREIGN PATENT DOCUMENTS 54-109907 8/1979 Japan .

Primary Examiner—Howard T. Mars

[57] ABSTRACT

A novel process for the purification of an alkylene oxide adduct which has been prepared using halogen-containing metal catalysts and contains halogen-containing compounds and also metals as impurities comprises treating the alkylene oxide adduct which is to be purified with an excess of alkali metal compound and adjusting the pH of the alkaline mixture obtained to a value of at most 7 using an acid, with the proviso that the water content of the product mixture which is then present is at least 0.1% by weight, relative to the weight of the product. This product mixture is freed from water and other solvents, this resulting in the precipitation in coarse crystalline form of salts which are insoluble in the alkylene oxide adduct and which can be easily separated off to isolate the desired pure alkylene oxide adduct.

9 Claims, No Drawings

PROCESS FOR THE PURIFICATION OF ALKYLENE OXIDE ADDUCTS

The invention relates to a process for the purification of an alkylene oxide adduct which has been prepared using halogen-containing metal catalysts and contains halogen-containing compounds and also metals as impurities.

It has long been known that the alkoxylation of mono- or poly-hydric alcohols using halogen-containing metal catalysts, preferably from the group of antimony halides and tin halides (which, as a rule, are used in the form of $SbCl_5$ and $SnCl_4$) provides a significantly narrower molecular weight distribution in the oxyalkylate than is obtained using basic catalysts. However, this considerable advantage is accompanied by the disadvantage that the oxyalkylate contains the catalyst metals used, such as antimony and/or tin, and also inorganically and/or organically bonded halogen as particularly undesirable impurities.

Furthermore, a plurality of processes are already known which are concerned with the purification of the above-mentioned oxyalkylates. For instance, JP-A2-54/109907 (cf. Derwent Abstract CPI No. 72865B/40) describes a process for purifying alkylene oxide adducts prepared using tin tetrachloride as catalyst, the purification comprising treatment of the adduct (crude oxyalkylate) with a phosphate or with phosphoric acid in an amount of from 0.1 to 5% by weight, based on the weight of adduct, the tin tetrachloride which is present being converted into tin phosphate which can be filtered off. Although this process is relatively successful in eliminating tin from the crude oxyalkylate, it does not free the product from the said halogen compounds which are also particularly troublesome impurities.

As stated in the above-cited Japanese document, the relevant purification has also been attempted by treating the crude oxyalkylate with alkali metal compounds, but the desired purity was not achieved and the treated oxyalkylate was even cloudy, fluorescent and/or gave precipitates. These negative results are confirmed in two comparative experiments in which the alkylene oxide adduct to be purified has been stirred with a certain amount of potassium hydroxide, or of sodium methanolate, at 120° C. for 30 minutes in each case.

A process for the treatment of the relevant alkylene oxide adducts (crude oxyalkylate) has now been found by which a virtually complete elimination not only of metals such as antimony and/or tin but also halogen-containing compounds can be achieved. The process according to the invention also allows, in particular, the organically bonded halogen to be captured and removed. The product obtained according to the invention not only has the high purity described but also is clear in appearance and odorless.

The process according to the invention for the purification of an alkylene oxide adduct which has been prepared using halogen-containing metal catalysts and contains halogen-containing compounds and also metals as impurities comprises (a) bringing the alkylene oxide adduct which is to be purified into contact at elevated temperature with at least 1.05 times the stoichiometric amount, relative to the amount of halogen present in the adduct, of alkali metal compounds from the group consisting of oxides, hydroxides and alcoholates, (b) adjusting the pH of the alkaline product from step (a) to a maximum of 7 with an acid, with the proviso that the product then obtained contains at least 0.1% by weight of water, relative to the weight of product, (c) freeing the product obtained after steps (a) and (b) from water and other solvents for the salts which were formed in steps (a) and (b) and are insoluble in the alkylene oxide adduct, and (d) isolating the desired pure alkylene oxide adduct from the product obtained in step (c), this product comprising essentially alkylene oxide adduct and the abovementioned salts, by separating off the said salts.

The process according to the invention gives an alkylene oxide adduct which is virtually free from metals such as antimony and tin and also from inorganically and organically bonded halogen (organically bonded halogen, which accounts for the majority of the overall halogen content, is present in organic halogen compounds which result essentially from the halogenating action of halogen-containing catalysts on the organic compounds such as alcohol, polyol, alkylene oxide and the like). The product obtained according to the invention is also odorless and has a clear appearance. These results are all the more surprising since the above-cited Japanese document not only advises repeatedly against the use of alkali metal compounds alone as purifying agents, but also advises against the use of a combination of alkali metal compound (alkali metal hydroxide) and acid (phosphoric acid) which is said to result in a denatured adduct.

Step (a) of the process according to the invention preferably employs alkali metal hydroxides and alkali metal alcoholates of $C_1$ to $C_4$-alkanols, in particular of methanol and ethanol. As a rule, the alkali metals are potassium and sodium for convenience. The alkali metal compound is preferably used in 1.3 to 5 times the stoichiometric amount, relative to the amount of halogen in the adduct to be purified, (to be explicit, the halogen is as a rule chlorine). It is quite possible to use a still larger amount of alkali metal compound but generally not convenient to do so. Furthermore, the alkali metal compound is preferably used in the form of a solution, the preferred solvents being water, a $C_1$ to $C_4$-alkanol or a mixture of water and a $C_1$ to $C_4$-alkanol. Particular preference is given to methanol or ethanol as the alkanol. If water and alcohol are used as the solvent, the ratio by weight of these two components may vary within wide limits; for example, the ratio may be in the range from 1:99 to 99:1 and is generally in the range from 1:70 to 70:1. Likewise, the concentration of alkali metal compound in the solutions is not crucial. For convenience, it is 1 to 70% by weight, preferably 5 to 50% by weight, relative to the weight of the aqueous, alcoholic or aqueous/alcoholic solution. In a preferred embodiment of step (a), the treatment of the crude oxyalkylate with the alkali metal compound is carried out by stirring the mixture of the crude oxyalkylate and the alkali metal compound at elevated temperature, preferably at a temperature from 80° to 180° C., in particular at 100° to 150° C., for 0.5 to 5 hours, preferably while maintaining an inert gas atmosphere, for example a nitrogen atmosphere, so as to exclude oxygen. Step (a) of the process according to the invention converts, for example, antimony into antimonate and tin into stannate and all of the inorganic and organically bonded halogen into alkali metal halide (this as a rule being sodium chloride or potassium chloride).

Step (b) of the process according to the invention mixes the crude oxyalkylate mixture obtained after carrying out step (a) with an acid, preferably with stirring, until the pH is at most 7, preferably from 3 to 7, in particular from 4 to 6.5. Acidification can be carried out using inorganic or organic acids and also the acid salts thereof, such as alkali metal salts, amine salts or ammonium salts. Preference is given to acids from the group consisting of the phosphorus acids, the sulfur acids, oxalic acid and citric acid, and particular preference is given to the phosphorus acids, sulfur acids and oxalic acid. From the group of phosphorus acids, preference is given to the use of phosphoric acid ($H_3PO_4$), phosphorous acid ($H_3PO_3$) and hypophosphorous acid ($H_3PO_2$) and from the group of sulfur acids, preference is given to the use of sulfuric acid ($H_2SO_4$) and sulfurous acid ($H_2SO_3$). The acid can be used as such or in dilute form, preferably in the form of a 20 to 90% by weight aqueous solution. The relevant acidification can be carried out at room temperature or at elevated temperature. Preferably a temperature of 20° to 150° C. is employed, and in particular a temperature of 50° to 130° C. Adjusting the pH as described ensures that antimonate and stannate, for example, and the excess of alkali metal hydroxide and/or alcoholate are converted into the corresponding salt of the acid used.

After adjustment of the pH, the mixture obtained must have a water content of at least 0.1% by weight, preferably of 0.5 to 10% by weight, the percentages by weight being relative to the weight of the mixture. This water content can be achieved for example by using, in step (a), an aqueous or aqueous/alcoholic solution and/or by acidifying in step (b) with an aqueous acid solution. If water is not introduced into the crude oxyalkylate either in step (a) or in the said acidification in step (b), (and therefore virtually no water is present), the required amount of water must then be added, i.e. before carrying out step (c).

Step (c) of the process according to the invention frees the product mixture, as obtained from step (b), from the solvents (in which the salts which are present are partly or entirely dissolved). These solvents are essentially water and alcohol, in particular water. Removal of the water and optionally of the alcohol is preferably carried out by distillation. The elimination of solvents by distillation can be carried out by heating the mixture, preferably to 100° to 130° C. with or without the assistance of a vacuum, and the distillation can be speeded up by using a carrier gas (nitrogen). A high vacuum allows removal of the solvent even at room temperature. As a rule, removal of the water is accompanied by the release from the mixture of other volatile components, for example the abovementioned alcohols.

After removal of water and alcohol from the mixture, all of the salts which are insoluble in the alkylene oxide adduct are present in a crystalline form of the type suitable for easy and complete separation from the alkylene oxide adduct. The requirement for the presence of water in the product mixture before it is treated in step (c) is based on the observation that the relevant salts are obtained in relatively coarse crystalline form, and so are readily and completely separable, if they are at least partly crystallized from water. The amount of water in the product mixture does not need to be so great that the total amount of the salts present are dissolved in it; on the other hand, it is possible to use much more water than is required for dissolving the whole quantity of salts. The amount of water used is preferably between about 0.5 to 10% by weight, the percentages by weight being based on the weight of the product mixture. It is quite possible to use a larger amount of water than the stated 10% by weight but it is inconvenient to do so since there is then more water to eliminate in step (c). A coarse crystalline salt is obtained in step (c) in both cases, i.e. with relatively little water or with a relatively large amount of water.

Step (d) of the process according to the invention separates off the compounds crystallized out in step (c). This separation, and isolation of the desired highly pure alkylene oxide adduct is preferably carried out by filtration or centrifugation of the product mixture. If the product mixture is solid or highly viscous at room temperature, the said separation is obviously carried out at a temperature at which the alkylene oxide adduct has the required flowability.

The type and composition of the alkylene oxide adduct which is treated by the process according to the invention are not crucial. The purification process according to the invention can be applied to various crude oxyalkylates. As a rule, these are customary oxyalkylates such as are obtained by oxyalkylation, preferably ethoxylation and/or propoxylation of compounds having at least one active hydrogen atom, preferably of monohydric or polyhydric alcohols. Suitable monohydric and polyhydric alcohols are alkanols (straight-chain or branched) having preferably 4 to 18 carbon atoms, ethylene glycol, propylene glycol, diethylene glycol, dipropylene glycol, butanediol, neopentyl glycol, glycerol, trimethylolpropane, erythritol, pentaerythritol, pentitols and hexitols and also the ($C_1$ to $C_{12}$-alkyl) partial ethers of the above polyhydric alcohols. Preference is given to alkanols and glycerol, ethylene glycol and propylene glycol and also to the to ($C_1$ to $C_{12}$-alkyl) partial ethers thereof. The process according to the invention is therefore preferably applied to crude oxyalkylates which have been prepared from the abovementioned monohydric or polyhydric alcohols by ethoxylation with 1 to 30 mol, preferably 2 to 20 mol, of ethylene oxide per mol of OH functional group in the alcohol, propoxylation with 1 to 30 mol, preferably 2 to 20 mol, of propylene oxide per mol of OH functional group in the alcohol or by ethoxylation with the said amount of ethylene oxide and propoxylation with the said amount of propylene oxide (using the relevant catalysts), particular preference being given to the abovementioned ethoxylates.

The invention is now explained in more detail using Examples.

Example 1

A $C_{18}$-alcohol ethoxylate having 2 mol of ethylene oxide per mol of alcohol is prepared using $SnCl_4$ catalysis by first charging a stirred autoclave with 560 g (2.0 mol) of dry octadecanol and admixing, at 40° to 60° C. and under an atmosphere of $N_2$, 1.6 g of $SnCl_4$ as catalyst. To this mixture are metered in 176 g of ethylene oxide (4.0 mol) in the course of 4 hours at 50° to 80° C. The initially exothermic reaction is brought to completion, (which is recognizable by a constant pressure being reached in the autoclave), by subsequent stirring for one hour at 80° C. The crude oxyalkylate has a chlorine content (which is essentially organically bonded chlorine) of 0.25% by weight and an Sn content of 0.20% by weight.

Purification of the crude oxyalkylate 8.6 g of sodium methanolate solution (30% by weight solution of CH₃ONa in methanol) are added under an atmosphere of N₂ to 500 g of the crude oxyalkylate in a stirred autoclave and the mixture is stirred for 1 hour at 130° C. The amount of sodium methanolate added is twice the stoichiometric amount, relative to the total chlorine present. After cooling the mixture to 70° C., 2.5 g of water are added and then the pH of the mixture is adjusted at the given temperature to 6.5 using 85% by weight aqueous phosphoric acid solution. The mixture contains 0.6% by weight of water (percentages by weight relative to the weight of mixture). The volatile components (water and methanol) of the mixture are then distilled off under reduced pressure (water pump vacuum) at 90° C. over a period of 45 minutes. The final step comprises separating off the salts, which are in coarse crystalline form, by hot filtration of the mixture. The ethylene oxide adduct purified in this way has a chlorine content of only 0.0011% by weight. The tin content is 0.0003% by weight (cf. the table below in which all of the examples are summarized with regard to the operation of the process and the result).

Example 2

A $C_{12/14}$-alcohol ethoxylate having 8 mol of ethylene oxide per mol of alcohol is prepared using $SbCl_5$ catalysis by first charging a stirred autoclave with 194 g (1.0 mol) of dry $C_{12/14}$-alcohol and admixing, under an atmosphere of N₂, 0.9 g of $SbCl_5$ as catalyst at 40° to 60° C. The above alcohol is converted using 352 g of ethylene oxide (8.0 mol) and the reaction of the ethylene oxide brought to completion, as under the same conditions described for Example 1.

Purification of the crude oxyalkylate 11.0 g of 25% by weight aqueous sodium hydroxide solution are added under an atmosphere of N₂ to 500 g of the crude oxyalkylate in a stirred autoclave and the mixture is stirred for 2 hours at 120° C. The amount of sodium hydroxide added is five times the stoichiometric amount, relative to the total chlorine present. After cooling the mixture to 90° C., the pH is adjusted to 4 using 50% by weight aqueous phosphoric acid solution. The water content of the mixture is 2.5% by weight. The volatile components (water) are then distilled off and the pure oxyalkylate is isolated by filtering the salts, which are present in coarse crystalline form, by the method described in Example 1.

Example 3

A glycerol-ethylene oxide-propylene oxide mixed oxyalkylate is prepared using $SbCl_5$ catalysis by first charging a stirred autoclave with 92 g (1.0 mol) of dry glycerol and admixing, under an atmosphere of N₂, 1.3 g of $SbCl_5$ as catalyst at 40° to 60° C. To this mixture is metered in a mixture of 264 g of ethylene oxide (6.0 mol) and 264 g of propylene oxide (4.5 mol) at 60° to 80° C. in the course of 5 hours. The oxyalkylation reaction is further carried out as in Example 1.

Purification of the crude oxyalkylate 11.9 g of sodium methanolate solution (30% by weight in methanol) are added under an atmosphere of N₂ to 500 g of the crude oxyalkylate in a stirred autoclave and the mixture is stirred for 1 hour at 140° C. The amount of sodium methanolate added is four times the stoichiometric amount, relative to the total amount of chlorine present. After cooling the mixture to 95° C., 5 g of water are added and the pH is adjusted to 6.3 using 50% by weight aqueous $H_2SO_4$ solution. The water content of the mixture is 1.5% by weight. Removal of the volatile components and filtration are carried out as in Example 1.

Example 4

A n-butanol ethoxylate having 15 mol of ethylene oxide per mol of butanol is prepared using $SbCl_5$ catalysis by reacting 74 g of dry n-butanol (1.0 mol) with 660 g of ethylene oxide (15.0 mol) in the presence of 2.4 g of $SbCl_5$ under the conditions described in Example 1.

Purification of the crude oxyalkylate 27.3 g of 8.4% by weight aqueous potassium hydroxide solution and 5 g of ethanol are added under an atmosphere of N₂ to 500 g of the crude ethoxylate in a stirred autoclave and the mixture is stirred for 2 hours at 140° C. The amount of potassium hydroxide added is 1.5 times the stoichiometric amount, relative to the total chlorine present. After slight cooling, the pH of the mixture is adjusted to 5 using oxalic acid dissolved in 10 g of water. The water content of the mixture is 7.0% by weight. Removal of the volatile components and filtration are carried out as described in Example 1.

Example 5

A $C_{12}$-alcohol ethoxylate having 4 mol of ethylene oxide per mol of alcohol is prepared using $SbCl_5$ catalysis by reacting 372 g (2.0 mol) of dry dodecanol with 352 g of ethylene oxide (8.0 mol) in the presence of 1.8 g of $SbCl_5$ under the conditions described in Example 1.

Purification of the crude oxyalkylate 8.4 g of 40% by weight aqueous potassium hyroxide solution are added under an atmosphere of N₂ to 500 g of the crude oxyalkylate in a stirred autoclave and the mixture is stirred for 2 hours at 130° C. The amount of potassium hydroxide added is twice the stoichiometric amount, relative to the total chlorine present. After cooling the mixture to 50° C., the pH is adjusted to 4.5 using 85% by weight aqueous phosphoric acid. The water content of the mixture is 2.8% by weight. Removal of the volatile components and filtration are carried out as described in Example 1.

Example 6

A $C_{12}$-alcohol ethoxylate having 8 mol of ethylene oxide per mol of alcohol is prepared using $SnCl_4$ catalysis by reacting 372 g (2.0 mol) of dry dodecanol with 704 g of ethylene oxide (16.0 mol) in the presence of 3.1 g of $SnCl_4$ under the conditions described in Example 1.

Purification of the crude oxyalkylate 7.1 g of 25% by weight aqueous sodium hydroxide solution are added under an atmosphere of N₂ to 500 g of the crude oxyalkylate in a stirred autoclave and the mixture is stirred for 4 hours at 110° C. The amount of sodium hydroxide added is twice the stoichiometric amount, relative to the total chlorine present. After cooling the mixture to 100° C., the pH is adjusted to 6.5 using 85% by weight aqueous phosphoric acid. The mixture has a water content of 1.0% by weight. Removal of the volatile components and filtration are carried out as described in Example 1.

Comparative Example A

Purification of the crude ethoxylate from Example 5

1.0 g of $Na_2HPO_4$ and 1.0 g of water are added to 200 g of the crude ethoxylate. The mixture is stirred for 2 hours at 120° C., and is then filtered to isolate the ethoxylate.

Comparative Example B

Purification of the crude ethoxylate from Example 6

1.4 g of $Na_2CO_3$ and 12 g of water are added to 200 g of the crude ethoxylate and the mixture is stirred for 4 hours at 105° C. Then the volatile components are distilled off under reduced pressure at a temperature of up to 90° C., and then the mixture is filtered to isolate the ethoxylate.

As already mentioned, the table which follows summarizes all the examples and the two comparative examples with regard to the operation of the process and the purification achieved.

TABLE

|  | Example 1 | Example 2 | Example 3 | Example 4 | Example 5 | Example 6 | Comparative Example A | Comparative Example B |
| --- | --- | --- | --- | --- | --- | --- | --- | --- |
| Alkanol or polyol | $C_{18}$-alcohol | $C_{12/14}$-alcohol | Glycerol | Butanol | $C_{12}$-alcohol | $C_{12}$-alcohol | $C_{12}$-alcohol | $C_{12}$-alcohol |
| mol Epoxide/mol | 2 EO | 8 EO | 6 EO/4.5 PO | 15 EO | 4 EO | 8 EO | 4 EO | 8 EO |
| Catalyst | $SnCl_4$ | $SbCl_5$ | $SbCl_5$ | $SbCl_5$ | $SbCl_5$ | $SnCl_4$ | $SbCl_5$ | $SnCl_4$ |
| Chlorine content (% by weight) | 0.25 | 0.10 | 0.12 | 0.20 | 0.15 | 0.16 | 0.15 | 0.16 |
| Sb or Sn content (% by weight) | 0.20 Sn | 0.07 Sb | 0.08 Sb | 0.14 Sb | 0.10 Sb | 0.13 Sn | 0.10 Sb | 0.13 Sn |
| Type of alkali | $CH_3ONa$ | NaOH | $CH_3ONa$ | KOH | KOH | NaOH | $Na_2HPO_4$ | $Na_2CO_3$ |
| Stoichiometric excess, relative to chlorine | 2 fold | 5 fold | 4 fold | 1.5 fold | 2 fold | 2 fold | — | 1.5 fold |
| Reaction temperature/time | 130° C./1 h | 120° C./2 h | 140° C./1 h | 140° C./2 h | 130° C./2 h | 110° C./4 h | 120° C./2 h | 105° C./4 h |
| Acid | $H_3PO_4$ | $H_3PO_3$ | $H_2SO_4$ | Oxalic acid | $H_3PO_4$ | $H_3PO_4$ | — | — |
| pH | 6.5 | 4 | 6.3 | 5 | 4.5 | 6.5 | 5.9 | 9.0 |
| Water content of the mixture (% by weight) | 0.6 | 2.5 | 1.5 | 7.0 | 2.8 | 1.0 | 0.5 | 6.0 |
| Result of the purification: |  |  |  |  |  |  |  |  |
| Chlorine content (% by weight) | 0.0011 | 0.0012 | 0.0020 | 0.0010 | 0.0015 | 0.0008 | 0.1500 | 0.1200 |
| Sb or Sn content (% by weight) | 0.0003 | <0.0001 | 0.0008 | <0.0001 | 0.0002 | 0.0002 | 0.0130 | 0.0002 |

As shown by the examples and comparative examples, the process according to the invention gives unexpectedly pure products not only with regard to the halogen content but also with regard to the metal content.

We claim:

1. A process for the purification of an alkylene oxide adduct which has been prepared using halogen-containing metal catalysts and contains halogen-containing compounds and also metals as impurities, which comprises
   (a) bringing the alkylene oxide adduct which is to be purified into contact at elevated temperature with at least 1.05 times the stoichiometric amount, relative to the amount of halogen present in the adduct, of an alkali metal compound from the group consisting of oxides, hydroxides and alcoholates,
   (b) adjusting the pH of the alkaline product from step (a) to a maximum of 7 with an acid, with the proviso that the product then obtained contains at least 0.1% by weight of water, relative to the weight of product,
   (c) freeing the product obtained after steps (a) and (b) from water and other solvents for the salts which were formed in steps (a) and (b) and are insoluble in the alkylene oxide adduct, and
   (d) isolating the desired pure alkylene oxide adduct from the product obtained in step (c), this product comprising essentially alkylene oxide adduct and the abovementioned salts, by separating off the said salts.

2. The process as claimed in claim 1, wherein step (a) employs an alkali metal hydroxide or an alkali metal $C_1$ to $C_4$-alcoholate.

3. The process as claimed in claim 1, wherein step (a) employs the alkali metal compound in 1.3 to 5 times the stoichiometric amount.

4. The process as claimed in claim 1, wherein step (a) employs the alkali metal compounds in the form of an aqueous, $C_1$ to $C_4$-alcoholic or $C_1$ to $C_4$-alcoholic/aqueous solution.

5. The process as claimed in claim 1, wherein the pH in step (b) is adjusted to at most 7, with the proviso that the product which is then present has a water content of 0.5 to 10% by weight.

6. The process as claimed in claim 1, wherein the pH in step (b) is adjusted using an acid from the group consisting of phosphorus acids, sulfur acids, oxalic acid and citric acid.

7. The process as claimed in claim 1, wherein step (a) brings the alkylene oxide adduct which is to be purified into contact with the alkali metal compound at a temperature of 80° to 180° C. and for 0.5 to 5 hours and step (b) adjusts the pH, using the acid, at a temperature of 20° to 150° C.

8. The process as claimed in claim 1, wherein
   (a) an alkali metal hydroxide or an alkali metal $C_1$ to $C_4$-alcoholate is added in an amount of 1.3 to 5 times the stoichiometric amount in the form of an aqueous, $C_1$ to $C_4$-alcoholic or $C_1$ to $C_4$-alcoholic/aqueous solution to the alkylene oxide adduct which is to be purified and the mixture is stirred for 0.5 to 5 hours at a temperature of 80° to 180° C.,
   (b) the alkaline product from step (a) is brought to a temperature of 20° to 150° C. and its pH is adjusted to 3 to 7 at this temperature using an acid from the group consisting of phosphorus acids, sulfur acids, oxalic acid and citric acid, with the proviso that the water content of the product which is then present is at least 0.1% by weight,
(c) the product obtained from steps (a) and (b) is freed from the solvents water and $C_1$ to $C_4$-alcohol by distillation, and
(d) the product obtained in step (c) is filtered or centrifuged.

9. The process as claimed in claim 1, wherein
(a) an alkali metal hydroxide or an alkali metal $C_1$ to $C_4$-alcoholate is added in an amount of 1.3 to 5 times the stoichiometric amount in the form of an aqueous, $C_1$ to $C_4$-alcoholic or $C_1$ to $C_4$-alcoholic-/aqueous solution to the alkylene oxide adduct which is to be purified and the mixture is stirred for 0.5 to 5 hours at a temperature of 100° to 150° C.,
(b) the alkaline product from step (a) is brought to a temperature of 50° to 130° C. and its pH is adjusted to 3 to 7 at this temperature using an acid from the group consisting of phosphorus acids, sulfur acids and oxalic acid, with the proviso that the water content of the product which is then present is 0.5 to 10% by weight,
(c) the product obtained from steps (a) and (b) is freed from the solvents water and $C_1$ to $C_4$-alcohol by distillation, and
(d) the product obtained in step (c) is filtered or centrifuged.

* * * * *